United States Patent [19]

Nilsson et al.

[11] 4,379,461

[45] Apr. 12, 1983

[54] THERMOGRAPHIC APPARATUS

[76] Inventors: Erling S. Nilsson, Vitmåravägen 77, Upplands Väsby; Staffan G. Zetterquist, Vesslevägen 4, Täby, both of Sweden

[21] Appl. No.: 204,366

[22] PCT Filed: Jan. 17, 1980

[86] PCT No.: PCT/SE80/00014

§ 371 Date: Sep. 17, 1980

§ 102(e) Date: Sep. 8, 1980

[87] PCT Pub. No.: WO80/01514

PCT Pub. Date: Jul. 24, 1980

[30] Foreign Application Priority Data

Jan. 17, 1979 [SE] Sweden .............................. 7900434

[51] Int. Cl.$^3$ .......................... A61B 5/00; A61B 5/02
[52] U.S. Cl. .............................. 128/736; 346/33 ME; 346/33 TP; 374/112; 374/124; 374/137
[58] Field of Search .............. 128/736; 73/343.5, 344, 73/340, 341; 346/33 ME, 33 TP

[56] References Cited

U.S. PATENT DOCUMENTS

| | | | |
|---|---|---|---|
| 2,967,939 | 1/1961 | Caha et al. | 346/33 ME |
| 3,306,282 | 2/1967 | Pierce | 128/736 |
| 3,877,463 | 4/1975 | Cary et al. | 128/2 H |
| 3,970,074 | 7/1976 | Mogos et al. | 128/736 |
| 3,980,073 | 9/1976 | Shaw | 128/736 X |
| 4,182,312 | 1/1980 | Mushabac | 128/776 X |

FOREIGN PATENT DOCUMENTS

| | | |
|---|---|---|
| 1383744 | 2/1975 | United Kingdom . |
| 1515538 | 6/1978 | United Kingdom . |
| 1240018 | 7/1979 | United Kingdom . |

OTHER PUBLICATIONS

Gould, Inc., Data Display, vol. 1, No. 2, p. 7.

Primary Examiner—Kyle L. Howell
Assistant Examiner—John C. Hanley
Attorney, Agent, or Firm—Browdy and Neimark

[57] ABSTRACT

The invention relates to a thermographic apparatus intended in particular for diagnosing disturbances in circulation in the extremities of a patient, by recording the temperature distribution along a selected line extending from the ankle of a patient up to the thigh on both legs of the patient, whereafter any asymmetry in the two registered temperature profiles is used for the basis of a diagnosis. The apparatus comprises a temperature transducer (4), preferably an IR-detector, which is carried on one end of an extendable and retractable arm (6), so that the transducer can be moved manually along a selected line on the leg (2) of the patient. Coupled to the arm (6) is a position transducer (11) for generating an electric signal representative of the distance moved by the temperature transducer. The apparatus also includes a recorder (10) to which both the temperature signal and the position signal are transmitted and which is arranged to record the measured temperature profile simultaneously. This sequence can be repeated on the other leg of the patient, so that the recorder records both temperature profiles. The apparatus also includes a signal-processing unit (14a, 14b) in which the analogue temperature signals and position signals are converted to digital form and stored so that they can later be processed in a calculator part (14c) which calculates the difference between the temperatures in mutually corresponding locations on the two legs of the patient, whereby a temperature difference-position-relationship is obtained, which after being converted to analogue form can be transmitted to the recorder (10) and recorded thereby.

7 Claims, 3 Drawing Figures

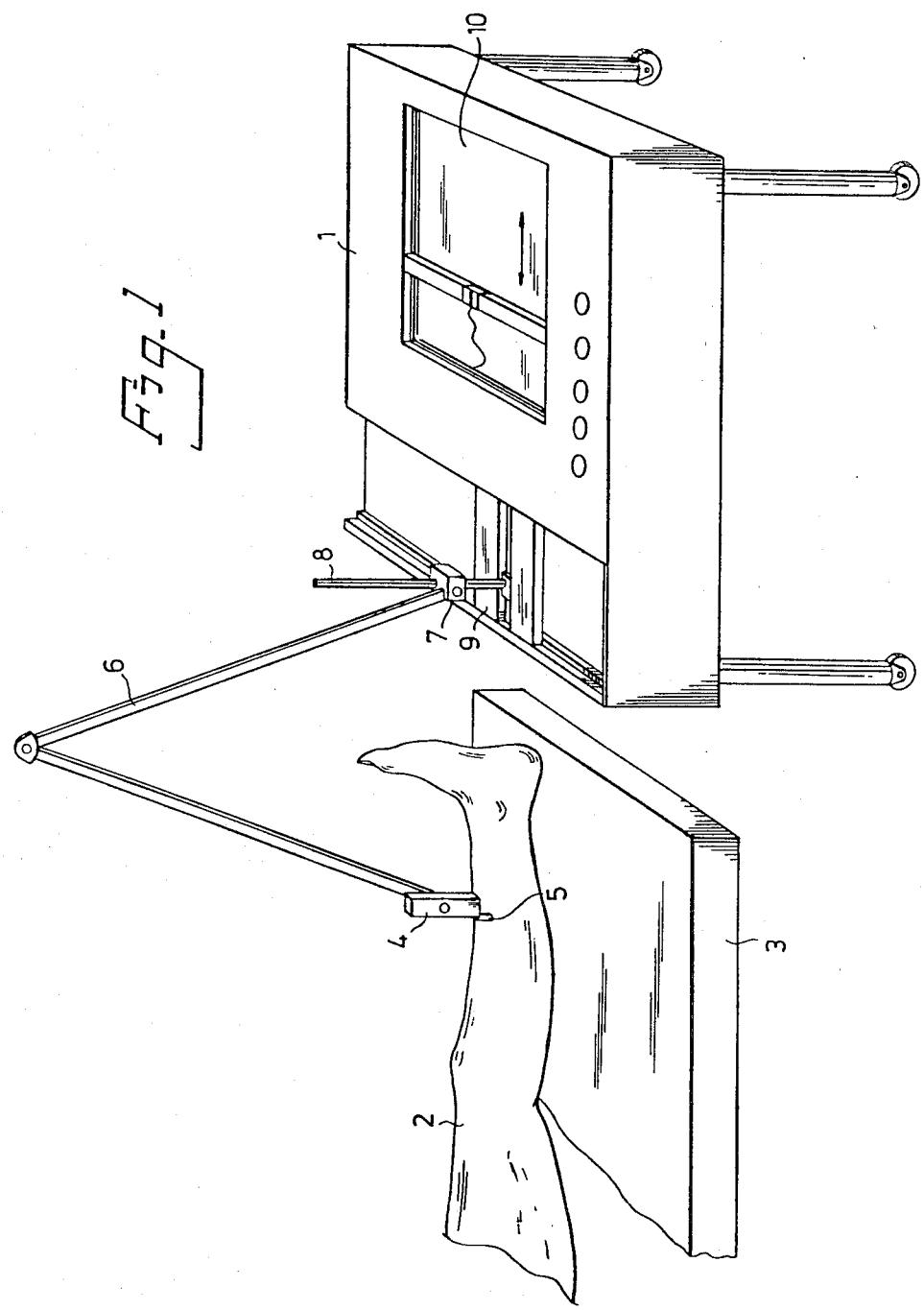

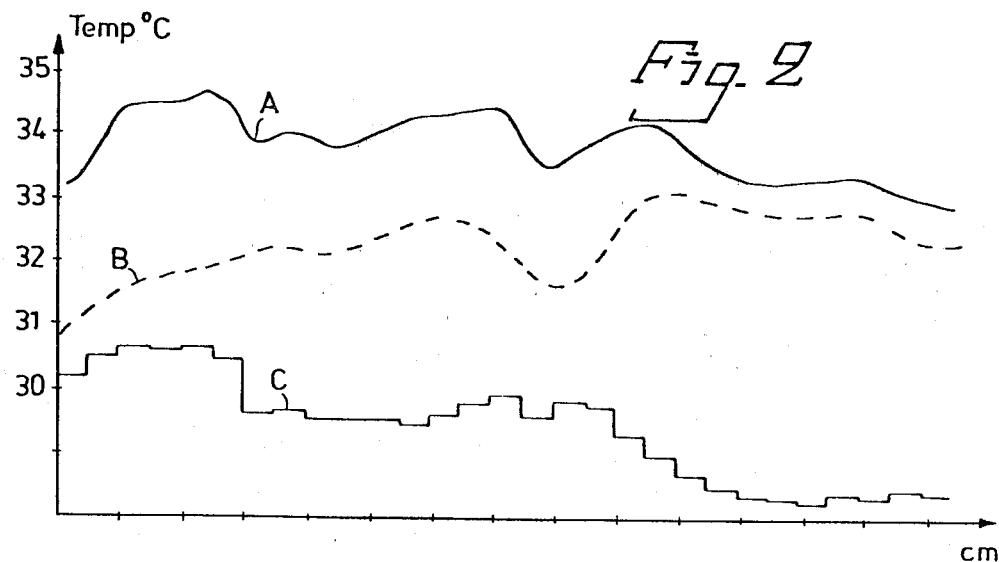
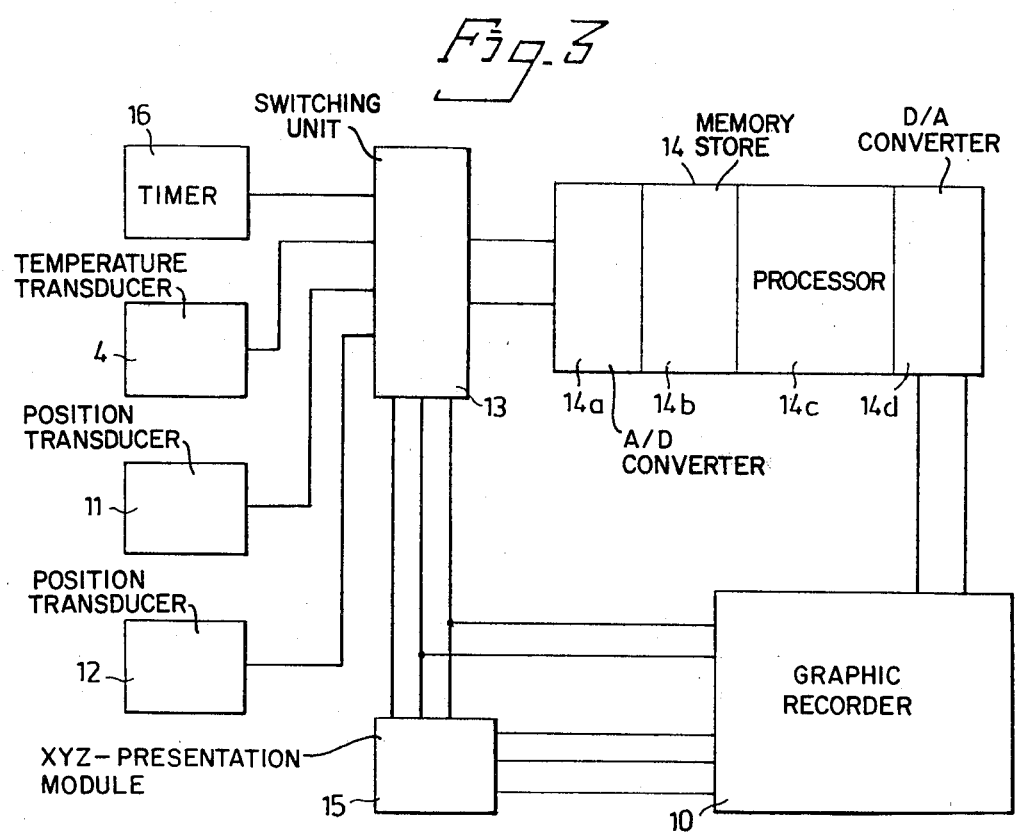

THERMOGRAPHIC APPARATUS

FIELD OF INVENTION

The present invention relates to apparatus for use in medical thermography for diagnostic purposes, i.e. for determining and registering the temperature of the surface of the skin of a patient, and in particular for detecting disturbances in the circulation in the limbs of a patient, such as the occurrence of deep venous thrombosis or arterial embolisms.

BACKGROUND OF THE INVENTION

It is well known that disturbances in the blood circulation in limbs causes the temperature of the skin to deviate from normal values. This fact has been utilized in diagnosing the aforementioned disorders in circulation, IR-scanning cameras being used to this end. Such cameras, however, are expensive and are relatively complicated in use, and hence a more comprehensive use of IR-scanning cameras for detecting and diagnosing disturbances in circulation by thermography is hardly conceivable.

SUMMARY OF THE INVENTION

The object of the present invention is therefore to provide an apparatus for thermographic diagnosis which is simpler, less expensive and more easily used than those apparatus used hitherto, and which is especially suited for the aforedescribed purpose.

The invention is based on a novel method of detecting and diagnosing disturbances in the circulation in a patient's leg, by measuring the temperature of the skin along a suitable line on each of the two legs of the patient and then comparing the two temperature curves thus obtained, any deviations or asymmetry between the two temperature curves indicating the presence of irregularities in the circulation in one or the other of said legs. Tests carried out in patients have shown that this thermographic method provides for the reliable diagnosis of the aforedescribed kind of disturbances in blood circulation.

The thermographic apparatus according to the invention is primarily constructed and intended for making thermographic examinations of the aforedescribed kind, although it can also be used for other thermographic examinations, as will be made clear hereinafter.

BRIEF DESCRIPTION OF THE DRAWINGS

An exemplary embodiment of the invention will now be described with reference to the accompanying drawings, in which FIG. 1 is a schematic illustration in perspective of an apparatus according to the invention, while being used to thermographically examine the leg of a patient;

FIG. 2 is a diagram illustrating by way of example temperature curves of the kind which can be obtained by means of an apparatus according to the invention when carrying out a thermographic examination of the aforedescribed kind; and FIG. 3 is a simplified block diagram of the construction of the signal-processing part of an apparatus according to the invention.

DETAILED DESCRIPTION OF PREFERRED EMBODIMENTS

FIG. 1 illustrates schematically a thermographic apparatus according to the invention, generally referenced 1, said apparatus in the illustrated embodiment comprising a roller table mounted on lockable rollers or wheels. The apparatus is illustrated in conjunction with examining the legs of a patient thermographically, in order to detect any irregularities of the circulation in the legs. For the sake of simplicity, only the left leg 2 of the patient is shown, said patient lying on an examination bed 3 or the like.

The apparatus according to the invention also includes a temperature transducer or sensor 4 of suitable kind arranged to sense the temperature of a closely adjacent surface, such as the surface of the skin of a part of a body, and to produce a corresponding electrical output signal. The temperature transducer 4 may, to advantage, be an infrared detector which when sensing the temperature of the surface of said skin need not be in direct contact therewith, but measures the temperature by detecting heat radiation transmitted from the surface of said skin within a given area. Infrared detectors which have variable focusing are known to the art, so that it is possible to vary the size of the area from which heat radiation is received and in which the temperature is thus measured. The temperature transducer 4 is, in the illustrated embodiment, suitably provided with a distance finger 5 or the like which may be held in contact with the surface of the skin during a temperature-measuring operation, such that the distance between said skin surface and the radiation detector in the temperature transducer 4 is hereby set to the correct value and remains constant.

The temperature transducer 4 is carried on one end of a knuckle arm 6, the other end of which is pivotally mounted on a holder 7, which is adjustable on a post 8 arranged on the table 1. The knuckle arm 6 is so arranged that the temperature transducer 4 can be moved along a desired line on the leg 2 of the patient, during which movement the transducer 4 delivers an electric temperature signal representative of the temperature of the skin along said line. Connected to the knuckle arm 6 is an electric position transducer (not illustrated), such as a linear potentiometer, said position transducer being connected in a manner to produce an electric output signal representative of the linear distance between the temperature transducer 4 and the opposite end 7 of said knuckle arm. Thus, this signal represents the extent to which the arm 6 has been extended, and therewith the relevant position of the temperature transducer 4 during its movement along the patient's leg.

The post 8 is mounted on a carriage or slide 9 capable of being moved on the table 1 in a direction perpendicular to the direction in which it is intended to extend the arm 6. The carriage 9 can be locked into selected positions and is suitably coupled to a further position transducer (not shown) arranged to generate electric output signals representative of the position of the carriage 9 or its displacement. As illustrated in the drawing, the post 8 may be arranged for movement on the carriage 9 in the direction in which the arm 6 is extended, so that said opposite end 7 of the arm 6 can be set to a selected position relative to the intended path of movement of the temperature transducer 4 during a temperature measuring operation.

In addition to the requisite operating and setting means for the operation and function of the apparatus, there is provided on the upper side of the table 1 a plotting table or graphic recorder 10 by means of which the temperature measured by the temperature transducer 4 can be recorded in thermogram form as a function of the position of said temperature transducer, e.g. as a function of the extent to which the arm 6 has been extended and therewith as a function of the distance moved by the temperature transducer 4 in the direction in which said arm 6 has been extended. The requisite electronic circuits for processing the generated signals are incorporated in the table 1.

As schematically illustrated in the block diagram of FIG. 3, the signal processing unit of the apparatus includes the aforementioned temperature transducer 4, the position transducer 11 which is connected to the arm 6 and which measures the distance through which the arm is extended, and the position transducer 12 which is connected to the carriage 9 and which senses the said position of said carriage. The analogue output signals from these transducer devices can be connected through a switching unit 13 to the graphic recorder 10 and to a signal-processing unit 14. The unit 14 comprises an A/D-unit 14a which converts the analogue signals received to corresponding digital signals; a memory store 14b for storing the digital signals; a processor or calculator 14c in which the signal data stored in the memory can be processed and subjected to mathematical calculations; and a D/A-unit 14d for converting the quantities calculated in the processor unit 14c to analogue signals which can be supplied to the recorder 10 for presentation.

The aforedescribed thermographic apparatus for thermographically examining the leg of a patient to ascertain whether there are irregularities in circulation, is used in the following manner:

The table 1 is positioned at the foot of the bed 3, on which the patient is placed in a substantially horizontal position, and the carriage 9 is positioned so that the post 8, and therewith the arm 6 and the temperature transducer 4, are located substantially opposite the line on one leg of the patient, along which the temperature of the skin is to be measured. The carriage 9 is locked in this position and the holder 7 is adjusted to a suitable height on the post 8. The temperature transducer 4 is positioned in a given location e.g. on the patient's ankle and is then moved manually along said line up the patient's leg to the upper regions of the thigh, while simultaneously depressing a suitable switch on the temperature transducer 4 so that the temperature signal T generated by the temperature transducer is passed to the apparatus table 1. At the same time, the position transducer 11 connected to the arm 6 generates an electric position signal X, which represents the distance through which the temperature transducer 4 has been moved along the leg. The temperature signal T generated by the temperature transducer 4, and the position signal X generated by the position transducer 11 are passed, through the switching element 13, to the recorder 10, which records the corresponding analogue temperature-position curve, e.g. the curve A in the diagram shown in FIG. 2. The analogue signals from said temperature transducer 4 and the position transducer 11 are also transmitted, through the switching element 13, to the signal-processing unit 14, in which the analogue signals are converted to digital signals in the A/D converter 14a, and the resultant digital signals are stored in the memory store 14b.

The carriage 9 is then moved on the table 1 to a position such that the arm 6 with the temperature transducer 4 is located opposite the corresponding sensing line on the other leg of the patient, whereafter a similar temperature-registering operation is carried out along said other leg. As a result hereof there is obtained a further temperature curve, such as the temperature curve referenced B in FIG. 2. The temperature signal from the transducer 4 and the position signal from the transducer 11 are also transmitted, through the switching unit 13, to the signal-processing unit 14, where the signals are converted to digital form and stored in the store 14b.

Thus, subsequent to measuring the skin temperature of the patient's legs in the aforedescribed manner, the two temperature profiles are stored in digital form in the memory store 14b of the apparatus. The processing unit 14c of the apparatus can now be initiated, to process said store data in a manner such that the temperature difference between corresponding locations on the two legs of the patient are determined as a function of position, i.e. the distance from the starting point at the ankles of the patient. This calculated temperature difference-position-relationship is converted in the D/A-converter 14d to corresponding analogue signals, which can be transmitted to the recorder 10, which then draws the curve C illustrated in the diagram in FIG. 2, said curve C indicating the temperature difference between the two legs of the patient as a function of the distance from the starting point, e.g. the ankles of the patient. On the basis of this temperature-difference curve it is possible to assess the occurrence and the position of any circulatory disturbances in the leg of the patient, e.g. disturbances in the form of venous thrombosis.

In the aforedescribed thermographic method using the apparatus according to the invention, no signal was used from the position transducer 12, which senses the position of the carriage 9. This position transducer 12 can be used, however, when it is desired to study the temperature distribution over a surface area, over a burn or leg ulcer for example. In this case, the temperature transducer 4 is moved by means of the arm 6 over the area of the skin in question, along a plurality of substantially mutually parallel spaced apart lines, the carriage 9 between each such linear scan being moved a distance which corresponds substantially to the distance between two adjacent scan lines. The signals obtained from the temperature transducer 4 and the two position transducers 11 and 12 are transmitted, through the switching unit 13, to a module 15 for analogue xyz-presentation, by means of which the recorder 10 is caused to simultaneously draw a family of curves which includes a temperature profile curve for each scan line, in a manner such as to obtain a "temperature topography" of the area scanned. Depending upon the capacity of the memory store and the design of the processor in the signal-processing unit 14, greater or lesser parts of the measuring data obtained when making such a scan of said surface can, of course, be stored and processed in a suitable, desired manner, e.g. for digital write-out or presentation by means of the recorder 10.

A device according to the invention may also be provided, to advantage, with a timer 16, which can be actuated to send to the switching means 13 an output signal representative of the time which has lapsed. In this way it is possible, by means of the apparatus according to the invention, to also register a temperature variation which is dependent on time, said temperature transducer 4 being held stationary at a given location on the area of the body whose temperature is to be studied as a function of time, and the temperature-time-sequence can be presented simultaneously in curve-form by means of the recorder 10 and also converted to digital form and stored in the unit 14 for further processing or evaluation. The registration of temperature as a function of time may be of interest in various provocation tests, e.g. cold-provocation when studying the circulation of hands and feet, and the influence on the circulation of different forms of nerve blockers.

By suitably designing the memory capacity and calculation routines of the signal-processing unit 14, an apparatus according to the invention can be constructed so as to enable it to be also used for other kinds of examinations than thermographic examinations, such as in particular occlusion plethysmography, which is a diagnostic method for deep venous thrombosis and which can be applied together with and complementary to the thermographic method described above. For the purpose of carrying out such occlusion plethysmographic operations, the apparatus according to the invention may be provided with two volume- or pressure sensors, which are applied at suitable locations on the extremity in question and the output signals of which are transmitted, through the switching means 13, to the signal-processing unit 14, together with a time signal from the timer 16, wherewith the processor 14c can be designed to calculate on the basis of this data such magnitudes as initial flow, the venous reserve volume and the emptying rate.

Although the illustrated and described embodiment of the apparatus according to the invention has only one temperature transducer with associated position transducer, it will be understood that said apparatus is not limited hereto, but may be provided with two or more temperature transducers with associated position transducers, so that a plurality of temperatures profiles can be registered simultaneously.

The illustrated and described exemplary embodiments of the apparatus can also be modified in other respects within the scope of the invention. Thus, the knuckle arm 6 can be replaced with another suitable kind of extendable and retractable arm for carrying the temperature transducer 4, such as a telescopic arm. Also other devices for determining the position of the temperature transducer and for generating a corresponding signal may be used, of course. Thus, the temperature transducer may e.g. be freely movable held only in the hand of the operator and connected to the end of a line or wire which can be pulled out from a winding device in the apparatus table, the position transducer consisting e.g. of a suitable revolution counter coupled to the winding device. The temperature transducer could also be completely free and its momentary position be determined optically or by means responsive to the movement of the transducer relative to the skin surface.

We claim:

1. An apparatus for detecting circulation disturbances in the legs of a patient by measuring and recording the skin surface temperature along the legs of the patient, comprising:
   at least one temperature sensor manually movable over the skin surface along the legs of a patient resting with his legs in a substantially horizontal position and capable of sensing the skin surface temperature of the momentarily adjacent portion of the patient's leg and generating an electric signal corresponding thereto;
   a movable apparatus frame structure adapted to be located at the feet of a patient under examination;
   means mechanically connecting said temperature sensor to said apparatus frame and including signal generating means responsive to the movement of said temperature sensor relative to said apparatus frame and for generating an electric signal representing the position of the temperature sensor along its path of movement;
   signal recording means mounted in said apparatus frame for receiving said temperature signal and said position signal and capable of recording the temperature being sensed as a function of the position of the temperature sensor; and
   digital signal processing means mounted in said apparatus frame for receiving said temperature and position signals and including data storing means for storing associated values of said temperature and position signals from at least two, different, measured temperature-position-relations and calculating means for comparing the temperature values as a function of the position for said two temperature-position-relations stored in said storing means and for producing signals representing the temperature difference as a function of the position for said two temperature-position relations, said recording means being capable of receiving said last mentioned signals for recording said temperature difference as a function of the position.

2. An apparatus as claimed in claim 1, wherein said mechanical connecting means comprise an extendable and retractable arm having one end mounted on said apparatus frame and an opposite end carrying said temperature sensor in a manner such that the temperature sensor can be moved linearly along the legs of the patient by extending or retracting said arm, and wherein said signal generating means responsive to the movements of the temperature sensor comprise a position transducer coupled to said arm for generating an electric signal representing the linear distance between said one end and said opposite end of said arm.

3. An apparatus as claimed in claim 2, further including:
   a carriage on which said one end of said extendable and retractable arm is supported, said carriage being mounted for movement on said apparatus frame in a direction substantially perpendicular to the direction in which the arm is extendable and provided with means for locking the carriage in a selectable position; and
   a second position transducer, coupled to said carriage, for generating a second electric position signal representative of the position of said carriage in its direction of displacement, wherein said recording means are capable of receiving also said second position signal and of recording the temperature being sensed as a function of both the extension of said arm and the position of said carriage.

4. An apparatus as claimed in claim 2, further including a substantially vertical post mounted on said apparatus frame, said arm being vertically adjustably mounted on said post.

5. An apparatus as claimed in claim 2, wherein said one end of said arm is displaceable on said apparatus frame in the direction in which the arm is extendable.

6. An apparatus as claimed in claim 1, further including a timer for generating an electric time signal, said signal recording means being capable of receiving said time signal and of recording the temperature being sensed as a function of time.

7. A method for detecting circulation disturbances in the legs of a patient by measuring and recording the skin surface temperature along the legs of the patient, using the apparatus in accordance with claim 1, comprising:
  placing said apparatus frame at the feet of a patient whose legs are horizontally disposed;
  moving said temperature sensor over the skin surface along one leg of the patient;
  recording the temperature being sensed as a function of the position of said sensor by means of said signal recording means;
  repeating said moving and recording steps with respect to the other leg of the patient; and
  recording the temperature differences between the two legs of the patient as a function of position by means of said digital signal processing means and said recording means.

* * * * *